US009457026B2

(12) United States Patent
Hiraoka et al.

(10) Patent No.: US 9,457,026 B2
(45) Date of Patent: Oct. 4, 2016

(54) METHODS FOR PRODUCING ARIPIPRAZOLE SUSPENSION AND FREEZE-DRIED FORMULATION

(75) Inventors: Shogo Hiraoka, Osaka (JP); Takakuni Matsuda, Osaka (JP); Junichi Hatanaka, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 428 days.

(21) Appl. No.: 12/670,352

(22) PCT Filed: Jul. 30, 2008

(86) PCT No.: PCT/JP2008/064076
§ 371 (c)(1),
(2), (4) Date: Apr. 23, 2010

(87) PCT Pub. No.: WO2009/017250
PCT Pub. Date: Feb. 5, 2009

(65) Prior Publication Data
US 2010/0196486 A1    Aug. 5, 2010

(30) Foreign Application Priority Data
Jul. 31, 2007 (JP) ................. 2007-200088

(51) Int. Cl.
| A61K 9/14 | (2006.01) |
| A61K 31/497 | (2006.01) |
| A61K 47/38 | (2006.01) |
| A61K 47/32 | (2006.01) |
| A61P 25/24 | (2006.01) |
| A61P 25/18 | (2006.01) |
| A61K 31/496 | (2006.01) |
| A61K 9/10 | (2006.01) |
| A61K 9/19 | (2006.01) |
| A61K 47/26 | (2006.01) |

(52) U.S. Cl.
CPC .............. *A61K 31/496* (2013.01); *A61K 9/10* (2013.01); *A61K 9/19* (2013.01); *A61K 47/26* (2013.01); *A61K 47/38* (2013.01)

(58) Field of Classification Search
None
See application file for complete search history.

(56) References Cited

U.S. PATENT DOCUMENTS

| 4,352,811 A | 10/1982 | Strupczewski et al. |
| 4,462,996 A | 7/1984 | Noda et al. |
| 4,652,811 A | 3/1987 | Kwiat et al. |
| 4,734,416 A | 3/1988 | Banno et al. |
| 4,804,663 A | 2/1989 | Kennis et al. |
| 5,006,528 A | 4/1991 | Oshiro et al. |
| 5,314,506 A | 5/1994 | Midler, Jr. et al. |
| 5,360,616 A | 11/1994 | Flores et al. |
| 5,510,118 A * | 4/1996 | Bosch et al. ................. 424/489 |
| 5,612,346 A | 3/1997 | Mesens et al. |
| 5,688,801 A | 11/1997 | Mesens et al. |
| 5,955,422 A | 9/1999 | Lin |
| 6,165,442 A | 12/2000 | Swaerd-Nordmo et al. |
| 6,267,989 B1 | 7/2001 | Liversidge et al. |
| 6,297,231 B1 | 10/2001 | Almarsson et al. |
| 6,455,526 B1 | 9/2002 | Kohn et al. |
| 6,482,518 B1 | 11/2002 | Short et al. |
| 6,495,164 B1 | 12/2002 | Ramstack et al. |
| 6,544,526 B1 | 4/2003 | Crabb et al. |
| 6,559,128 B1 | 5/2003 | Hamm et al. |
| 6,669,963 B1 | 12/2003 | Kampinga |
| 6,977,257 B2 | 12/2005 | Parab et al. |
| 6,987,111 B2 | 1/2006 | Greco et al. |
| 7,115,587 B2 | 10/2006 | Nerurkar et al. |
| 7,514,072 B1 | 4/2009 | Ehrenreich et al. |
| 7,541,021 B2 | 6/2009 | Sambuco et al. |
| 7,550,445 B2 | 6/2009 | Nerurkar et al. |
| 7,807,680 B2 | 10/2010 | Kostanski et al. |
| 2004/0156792 A1 * | 8/2004 | Tarara et al. .................. 424/46 |
| 2004/0209843 A1 | 10/2004 | Inoue et al. |
| 2004/0258757 A1 | 12/2004 | Bosch et al. |
| 2005/0032811 A1 | 2/2005 | Brown |
| 2005/0148597 A1 * | 7/2005 | Kostanski et al. ........ 514/253.07 |
| 2005/0220887 A1 * | 10/2005 | Herbert et al. ............... 424/489 |

(Continued)

FOREIGN PATENT DOCUMENTS

| EP | 0 072 662 A2 | 2/1983 |
| EP | 0 941 066 B1 | 9/1999 |

(Continued)

OTHER PUBLICATIONS

Specification sheet from Avestin for EmulsiFlex-C5, downloaded Mar. 15, 2012 from http://www.avestin.com/English/c5page.htm).*

(Continued)

*Primary Examiner* — Frederick Krass
*Assistant Examiner* — Michael P Cohen
(74) *Attorney, Agent, or Firm* — Finnegan, Henderson, Farabow, Garrett & Dunner, LLP

(57) ABSTRACT

Disclosed are a method for producing an aripiprazole suspension, wherein the aripiprazole has a mean particle size of 1 to 10 μm, the method comprising the steps of: (a) combining bulk aripiprazole and a vehicle to form a primary suspension; (b) subjecting the primary suspension to first pulverization using e.g., a high shear pulverizing machine, a dispersion machine that applies shear force to a material to be processed, a colloid mill, an ultrasonic dispersion machine, or a high-pressure jet type emulsifying dispersion machine to form a secondary suspension; and (c) subjecting the secondary suspension to second pulverization using e.g., a high-pressure jet type emulsifying dispersion machine to form a sterile final suspension; and a method for producing a freeze-dried formulation from the aripiprazole suspension.

20 Claims, No Drawings

(56) References Cited

U.S. PATENT DOCUMENTS

| | | | |
|---|---|---|---|
| 2007/0148100 A1* | 6/2007 | Jenkins | 424/46 |
| 2007/0148245 A1* | 6/2007 | Zalit et al. | 424/486 |
| 2008/0107745 A1 | 5/2008 | Kostanski et al. | |
| 2008/0112985 A1 | 5/2008 | Kostanski et al. | |
| 2008/0112986 A1 | 5/2008 | Kostanski et al. | |
| 2008/0221121 A1 | 9/2008 | Matsuda et al. | |
| 2008/0279928 A1* | 11/2008 | Moschwitzer | 424/455 |
| 2009/0186903 A1 | 7/2009 | Nerurkar et al. | |
| 2009/0274628 A1 | 11/2009 | Ottoboni et al. | |

FOREIGN PATENT DOCUMENTS

| | | |
|---|---|---|
| EP | 1 407 785 A1 | 4/2004 |
| EP | 1 675 573 B1 | 7/2006 |
| ES | 2 084 594 | 5/1996 |
| GB | 209551 | 2/1923 |
| GB | 2 095 551 A | 10/1982 |
| JP | 02-191256 A | 7/1990 |
| JP | 2001/187735 A | 7/2001 |
| JP | 2002 241284 A | 8/2002 |
| JP | 2003 063965 A | 3/2003 |
| JP | 2003-212852 A | 7/2003 |
| JP | 2003-531162 A | 10/2003 |
| JP | 2005-022989 A | 1/2005 |
| JP | 3750023 B2 | 12/2005 |
| JP | 3760264 B2 | 1/2006 |
| JP | 2007-509148 A | 4/2007 |
| JP | 2007-509153 A | 4/2007 |
| RU | 2 082 401 C1 | 6/1997 |
| RU | 2 104 692 C1 | 2/1998 |
| RU | 2 169 574 C1 | 6/2001 |
| WO | 92/10175 A1 | 6/1992 |
| WO | 95/13814 A1 | 5/1995 |
| WO | 95/33488 A1 | 12/1995 |
| WO | 99/12549 A2 | 3/1999 |
| WO | 99/49846 | 10/1999 |
| WO | 00-35475 A2 | 6/2000 |
| WO | 00/35475 A2 | 6/2000 |
| WO | 01/58428 A1 | 8/2001 |
| WO | 01/72297 A1 | 10/2001 |
| WO | 02/085366 A1 | 10/2002 |
| WO | 03/024426 A1 | 3/2003 |
| WO | 03/026659 A1 | 4/2003 |
| WO | 2004/006886 A2 | 1/2004 |
| WO | 2004/017897 A2 | 3/2004 |
| WO | 2004/054545 | 7/2004 |
| WO | 2004/064752 A2 | 8/2004 |
| WO | 2005/016262 A2 | 2/2005 |
| WO | 2005/041937 A2 | 5/2005 |
| WO | 2005/041970 A1 | 5/2005 |
| WO | WO 2005041937 A2 * | 5/2005 |
| WO | 2005/072702 A2 | 8/2005 |
| WO | WO 2006094808 A2 * | 9/2006 |
| WO | 2007 053904 A1 | 5/2007 |

OTHER PUBLICATIONS

Product brochure for Microfluidics International Corp. downloaded Mar. 16, 2010 from http://www.microfluidicscorp.com/images/stories/pdf/m-110eh-30.pdf.*
MSDS for acetic acid downloaded on Mar. 26, 2012 from http://www.sciencelab.com/msds.php?msdsld=9922769.*
Muller R.H., Benita, S., and Bohm, B. Emulsions and Nanosuspensions, Stuttgart: Medpharm, 1998, p. 185.*
M.J. Grau, O. Kayser, R.H. Muller. Nanosuspensions of poorly soluble drugs—reproducibility of small scale production. International Journal of Pharmaceutics 196 (2000) 155-157.*
Rainer H. Muller, Katrin Peters. Nanosuspensions for the formulation of poorly soluble drugs I. Preparation by a size-reduction technique. International Journal of Pharmaceutics 160 (1998) 229-237.*
Illig K J et al., "Use of Microfluidizer Processing for Preparation of Pharmaceutical Suspensions", Pharmaceutical Technology, Advanstar Communications, Eugene, Oregon, U.S., vol. 20, No. 10, Oct. 1996, pp. 78-88.
Satoshi Aoki et al., "Study on Crystal Transformation of ARIPIPRAZOL", The Fourth Japan-Korea Symposium on Separation Technology, Oct. 6-8, 1996, pp. 937-940.
Prescribing information for ABILIFY® (Aripiprazole).
Srinivas K.S., Buchireddy R., Madhusudhan G., Mukkanti K., Srinivasulu P., "Stress Degradation Studies on Aripiprazole and Development of a Validated Stability Indicating LC Method", Chromatographia, vol. 68, pp. 635-640 (2008).
Prescribing information for KENALOG®—10 Injection—triamcinolone acetonide injectable suspension, USP.
Prescribing information for DEPO-PROVERA® Contraceptive Injection—medroxyprogesterone acetate sterile aqueous suspension, 150 mg/mL, USP.
Nakamura, A. and Okada, R., "The coagulation of particles in suspension by freezing-thawing—I. Effect of freezing-thawing conditions and other factors on coagulation", Colloid & Polymer Sci., vol. 254, pp. 718-725 (1976).
Nakamura, A. and Okada, R., "The coagulation of particles in suspension by freezing-thawing—IV. Prevention of coagulation by network or eutectic formation", Colloid & Polymer Sci., vol. 255, pp. 362-367 (1977).
Clausi A.L., Merkley S.A., Carpenter J.F., Randolph T.W., "Inhibition of aggregation of aluminum hydroxide adjuvant during freezing and drying", Journal of Pharmaceutical Science, vol. 97, No. 6, pp. 2049-2061 (2008).
Heller, M.C., Carpenter, J.F. and Randolph, T.W., "Protein formulation and lyophilization cycle design: Prevention of damage due to freeze-concentration induced phase separation," Biotechnology & Bioengineering vol. 63, No. 2, pp. 166-174 (1999).
Franks F., "Freeze-drying of bioproducts: putting principles into practice", European Journal of Pharmaceutics and Biopharmaceutics, vol. 45, pp. 221-229 (1998).
Zapata, M.I., Peck, G.E., Hem, S.L., White, J.L., and Feldkamp, J.R., "Mechanism of freeze-thaw instability of aluminum hydroxycarbonate and magnesium hydroxide gels", Journal of Pharmaceutical Science, vol. 73, No. 1, pp. 3-8 (1984).
Nakamura, A. and Okada, R., "The coagulation of particles in suspension by freezing-thawing—II. Mechanism of coagulation", Colloid & Polymer Science, vol. 254, pp. 497-506 (1976).
Tsapis, N., Dufresne, E.R., Sinha, S.S., Riera, C.S., Hutchinson, J.W., Mahadevan, L., and Weitz, D.A., "Onset of Buckling in Drying Droplets of Colloidal Suspensions", Physics Review Letters, vol. 94, pp. 018302-1 to 018302-4 (2005).
Maa Y.F., Zhao L., Payne L.G., Chen D., "Stabilization of alum-adjuvanted vaccine dry powder formulations: Mechanism and application", Journal of Pharmaceutical Science, vol. 92, pp. 319-332 (2003).
Hirakura Y., Kojima S., Okada A., Yokohama S., Yokota S., "The improved dissolution and prevention of ampoule breakage attained by the introduction of pretreatment into the production process of the lyophilized formulation of recombinant human Interleukin-11 (rhIL-11)", International Journal of Pharmaceutics, vol. 286, Nos. 1-2, pp. 53-67 (2004).
Nakamura, A. and Okada, R., "The coagulation of particles in suspension by freezing-thawing—III. Prevention of coagulation by unfrozen water", Colloid & Polymer Science, vol. 255, pp. 343-356 (1977).
Clausi, A. et al, "Influence of Protein conformation and adjuvant aggregation on the effectiveness of aluminum hydroxide adjuvants in a model alkaline phosphatase vaccine," Journal Pharmaceutical Sciences, vol. 98, pp. 114-121 (2009).
Clausi, A. et al, "Influence of Particle Size and antigen binding on effectiveness of aluminum salt adjuvants in a model lysozyme vaccine," Journal of Pharmaceutical Sciences, vol. 97, pp. 5252-5262 (2008).
Chacon, M. et al, "Stability and freeze-drying of cyclosporine loaded poly(D,L lactide-glycolide) carriers," European Journal of Pharmaceutical Sciences, vol. 8, pp. 99-107 (1999).
Kwok, K. et al, "Strategies for maintaining the particle size of peptide DNA condensates following freeze-drying," International Journal of Pharmaceutics, vol. 203, pp. 81-88 (2000).

(56) References Cited

OTHER PUBLICATIONS

Perrin, J., "Freezing of Suspensions," American Journal of Hospital Pharmacy, vol. 36, pp. 1157, 1160 and 1163 (Sep. 1979).
Prescribing information for Center-Al® (Allergenic extracts, Alum Precipitated).
Prescribing information for CellCept® Oral Suspension (Roche).
Prescribing information for Kenalog®—40 Injection (triamcinolone acetonide injectable suspension, USP).
Prescribing information for Megestron® Suspension for injection 150 mg/ml (Organon).
Prescribing information for Novolin® 70/30—insulin human injection, suspension (Novo Nordisk).
Lee et al, "Cryoprotectants for Freeze Drying of Drug Nano-Suspensions: Effect of Freezing Rate", Journal of Pharmaceutical Sciences, vol. 98, No. 12, pp. 4808-4817 (Dec. 2009).
Abdelwahed et al, "Freeze-drying of nanoparticles: Formulation, process and storage considerations", Advanced Drug Delivery Reviews, vol. 58, pp. 1688-1713 (2006).
Chaubal and Popescu, "Conversion of Nanosuspensions into Dry Powders by Spray Drying: A Case Study," Pharmaceutical Research, vol. 25, No. 10, pp. 2302-2308 (Oct. 2008).
Van Eerdenbrugh et al, "Drying of crystalline drug nanosuspensions—The importance of surface hydrophobicity on dissolution behavior upon redispersion", European Journal of Pharmaceutical Sciences, vol. 35, pp. 127-135 (2008).
Nakamura, Akio, Hyomen, vol. 13, No. 1, pp. 1-10, published Jan. 1, 1975.
Remington, The Science and Practice of Pharmacy 19$^{th}$ ed., pp. 278-282 (1995).
Encyclopedia of Pharmaceutical Technology, vol. 6, pp. 3601-3602.
Pharmaceutical Dosage Forms: Disperse Systems, 2$^{nd}$ ed., vol. 2, p. 189 (Marcel Dekker, Inc. 1996).
Martin's Physical Pharmacy and Pharmaceutical Sciences, Physical Chemical and Biopharmaceutical Principles in the Pharmaceutical Sciences, 5$^{th}$ ed., p. 504.
Handbook of Pharmaceutical Excipients, American Pharmaceutical Association et al., publs., pp. v-vi (table of contents) 1986.
Lieberman et al. eds., Pharmaceutical Dosage Forms: Disperse Systems, vol. 1, pp. 153-163 (1998), Marcel Dekker Inc.
Gennaro et al. eds., Remington's Pharmaceutical Sciences, pp. 591-592 (1990), Mack Publishing Co.
Handbook of Pharmaceutical Excipients, pp. 45-48 (1986), American Pharmaceutical Association.
Nema et al, "Excipients and Their Use in Injectable Products", PDA J. of Pharm. Sci. & Tech., vol. 51, No. 4; pp. 166-171 (1997).
Edman, "Pharmaceutical Formulations-Suspensions and Solutions", Journal of Aerosol Medicine, vol. 7, Supplement 1, pp. S-3 to S-6 (1994).
Altamura, et al, "Intramuscular Preparations of Antipsychotices", Drugs, vol. 63, No. 5, pp. 493-512 (2003).
Zuidema et al., "Release and Absorption Rate Aspects of Intramuscularly Injected Pharmaceuticals", International Journal of Pharmaceutics, vol. 47, pp. 1-12 (1988).
Strickley et al, "Parenteral Formulations of Small Molecules Therapeutics Marketed in the United States" PDA J. of Pharm. Sci. & Tech., vol. 53, No. 6, pp. 324-349 (1999).
"Prostetin: Oxendolone Injectable Aqueous Suspension Formulation", Standard Commodity Classification No. of Japan 872499 (Jan. 1992).
Shoji, "Manufacture Technology of Solid Tablet", CMC Publishing Co., Ltd., pp. 138-141 (Mar. 5, 1985).
Midgley, et al, "The Metabolic Fate of the Anti-Androgenic Agent", Steroids, vol. 41, No. 4, Apr. 1983.
Masuoka et al., "Anti-Androgen TSAA-291" ACTA Endocrinologica, 92 (Suppl. 229), pp. 24-35 (1979).
Garza-Flores et al., "Assessment of a New Low-Dose Once-A-Month Injectable Contraceptive", Contraception, vol. 37, No. 5, pp. 471-481, May 1988.
Garza-Flores et al., Development of a Low-Dose Monthly Injectable Contraceptive System: I. Choice of Compounds, Dose and Administration Route:, Contraception, vol. 30, No. 4, pp. 371-379, Oct. 1984.
Diaz-Sanchez et al., "Development of a Low-Dose Monthly Injectable Contraceptive System: II. Pharmacokinetic and Pharmacodynamic Studies", Contraception, vol. 35, No. 1, pp. 57-68, Jan. 1987.
Nakagawa et al., "Derivatives of 3, 4-Dihydrocarbostyril as beta-adrenergic blocking agents", Journal of Medicinal Chemistry, vol. 17, No. 5, pp. 529-533, 1974.
Petigara et al., "Synthesis and Central Nervous System Depressant Activity of New Piperazine Derivatives, I", J. Med. Chem.; vol. 11, No. 2, pp. 332-336, 1968.
Fielden, et al., "Synthesis and Central Nervous System Depressant Activity of Some 5-(2-Substituted alkyl)-2-oxazolidinones", Journal of Medicinal Chemistry, vol. 16, No. 10, pp. 1124-1128, 1973.
The Pharmacological Basis of Therapeutics (Goodman and Gilman, Ed., 1975); pp. 47-53, 153-197 and 590-623.
Gennaro, "Remington: The Science and Practice of Pharmacy", 19th Edition, Mack Publishing Company 1995, pp. 1668-1671.
European Pharmacopoeia 6th Edition, published Jul. 16, 2007, p. 736.
Notice of Opposition, dated Jul. 22, 2009 to European Patent No. 1675573.
Search Report for Georgian Patent Application No. 9360012006, dated Oct. 8, 2009.
Office Action for Taiwanese Patent Application No. 93131836, dated Dec. 16, 2009.
Examination Report issued for Columbian Patent Application No. 06-36842, dated Jan. 8, 2010.
Akers et al., "Formulation Design and Development of Parenteral Suspension", Journal of Parenteral Science & Technology, vol. 41, No. 3, pp. 88-96, May-Jun. 1987.
Lieberman et al. eds., Pharmaceutical Dosage Forms: Disperse Systems, vol. 2, pp. 261-301 (1996), Marcel Dekker Inc.
Wade and Waller, eds. Handbook of Pharmaceutical Excipients (Second Edition), pp. 78-81, 1994, American Pharmaceutical Association.
Anne Paavola et al, Controlled release and dura mater permeability of lidocaine and ibuprofen from injectable poloxamer-based gels, Journal of Controlled Release, 1998, vol. 52, pp. 169-178.
Encyclopedia of Pharmaceutical Technology, edited by James Swarbrick, Third Edition, vol. 3, pp. 1884-1885.
Physicians' Desk Reference, Edition 51, 1997, pp. 1010-1011, 1710-1713, 2078-2081.
Depo-Medrol—Methylprednisolone Acetate Injectable Suspension, USP—Product Information, pp. 1-17 (Revised May 2008).
Kenalog—40 Injection—Triamcinolone Acetonide Injectable Suspension, USP—Product Information, pp. 1-20 (Revised Oct. 2006).
Alkermes, Inc.'s Opposition to European Patent No. 1675573 (EP Application No. 04795514.1), pp. 1-13 (Jul. 28, 2009).
Lieberman, Herbert A. et al, "Pharmaceutical Dosage Forms: Disperse Systems" 2nd Ed., vol. 2, pp. 261-301, New York, 1996.
Murata et al, "Pharmaceutics", pp. 98-101, Nankodo Co. Ltd., Japan, 1997.
Office Action dated Nov. 16, 2010 on Japanese Patent Application No. 2006-536693.
Merck Index 13$^{th}$, Merck & Co., N.J., U.S.A., 2001, No. 791.
Gennaro R. Alfonso, Remington, Farmacia, 19$^{th}$ Edition Panamericana, Spain, 1988, pp. 2337-2338.
Declaration of Daniel R. Deaver submitted in Alkermes's Japanese Patent Application No. 2006-522614.
Leon Lachman, Ph.D. et al, The Theory and Practice of Industrial Pharmacy, Third Edition, Indian Edition, 1987, pp. 644, 655 and 656.
Arthur H. Kibbe, Ph.D., editor, Handbook of Pharmaceutical Excipients, Third Edition, p. 664.
Declaration Under 37 CFR 1.132 of Stephen E. Zale submitted in U.S. Appl. No. 10/635,221 (Brown).
Michael J. Akers, Excipient-Drug Interactions in Parenteral Formulations, Journal of Pharmaceutical Sciences, vol. 91, No. 11, pp. 2283-2300 (Nov. 2002).

(56) References Cited

OTHER PUBLICATIONS

The British Journal of Radiology, 56, p. 897 (Nov. 1983).
Office Action dated Sep. 24, 2010 on U.S. Appl. No. 11/979,144.
Office Action dated Apr. 12, 2011 on Taiwanese Application No. 093131836.
Alkermes Controlled Therapeutics, Inc.'s submission dated Mar. 30, 2011 to the European Patent Office in Alkermes's opposition to Otsuka's Pharmaceutical Co., Ltd's European Patent No. 1,675,573.
Otsuka Pharmaceutical Co., Ltd.'s submission dated May 5, 2011 to the European Patent Office in Alkermes's opposition to Otsuka's European U.S. Pat. No. 1,675,573.
Otsuka Pharmaecutical Co., Ltd.'s response dated Mar. 8, 2010 to Alkermes Controlled Therapeutics, Inc.'s opposition to Otsuka's European Patent No. 1,675,573.
Office Action dated Jun. 30, 2011 on Chinese Application No. 200880100781.4.
Office Action dated Jun. 28, 2012 in Russian Application No. RU 2009149820.
V.I. Chueshov "Promyshlannaya tekhnologia lekarstv", Industrial technology of medicaments, vol. 1, 2002, p. 32.
Office Action dated May 9, 2013 in Israel Patent Application No. 203031.
Hecq et al., "Preparation and characterization of nanocrystals for solubility and dissolution rate enhancement of nifedipine", International Journal of Pharmaceutics, 2005, vol. 299, pp. 167-177.
Lieberman et al., Pharmaceutical Dosage Forms: Disperse Systems, vol. 3, second edition, 1998, pp. 274 and 343-345.

\* cited by examiner

METHODS FOR PRODUCING ARIPIPRAZOLE SUSPENSION AND FREEZE-DRIED FORMULATION

TECHNICAL FIELD

The present invention relates to a method for producing an aripiprazole suspension, and also a method for producing freeze-dried formulations.

BACKGROUND ART

Aripiprazole is a drug commonly known as an atypical antipsychotic agent. Using an aripiprazole aqueous suspension as an injectable formulation has been proposed for the administration of aripiprazole. In particular, a suspension obtained by suspending aripiprazole with a mean particle size of about 1 to about 10 μm in an aqueous vehicle is known to have excellent sustained-release properties and bioavailability (Patent Document 3).

In prior art, aseptic pulverization of bulk aripiprazole was difficult at the commercial production level. For example, a ball milling method, which uses ceramic beads widely used in wet milling, has problems: bead friction may cause contamination; additionally, ball mills capable of in-line sterilization are generally not commercially available currently.

Moreover, the ball mill pulverization method may possibly involve a problem of short-pass in which some large particles possibly slip through the beads. As shown in Patent Document 4, it is preferable to use bulk aripiprazole having a desired small particle size, preferably having a mean particle size of about 100 μm or less, more preferably about 95% of the crystals having a particle size less than 100 μm with a narrow particle size distribution. However, production of such bulk aripiprazole having a mean particle size of about 100 μm or less requires particular crystallization techniques like an impinging jet crystallization method, as described in Patent Document 4.

On the other hand, particle size reduction can be carried out using a high-pressure homogenizer; however, when a 10% suspension of aripiprazole having a mean particle size of more than 100 μm is pulverized with a high-pressure homogenizer, clogging occurs in the line, precluding pulverization. Therefore, it is desired to use aripiprazole preferably with a mean particle size of 100 μm or less.

However, suspending such aripiprazole with a mean particle size of about 100 μm or less in a vehicle solution is accompanied by foaming. Therefore, mixing under vacuum is necessary for the preparation of a homogeneous suspension (see Patent Document 3, Example 1 and paragraph 0089).

When mixing is carried out under vacuum, outside air may be introduced, which requires measures to prevent contamination from the external environment. Improvement in this aspect is desired.

Patent Document 1 discloses a method for preparing small particles containing a poorly water-soluble drug, comprising the steps of:

(a) mixing at high shear an admixture of a poorly water-soluble drug and one or more surface active substances in an aqueous carrier in the absence of an organic solvent within a first temperature range at or above the melting point of the poorly water-soluble drug to form a heated suspension containing the drug wherein the drug is molten;

(b) homogenizing the heated suspension in a first pressure range and within the first temperature range to form a heated homogenate containing the drug wherein the drug is molten;

(c) cooling the heated homogenate to a second temperature range below the melting temperature of the poorly water-soluble drug to form a transiently stable, cooled homogenate containing the drug;

(d) applying a particle stabilizing energetic process to the cooled homogenate within a second temperature range below the melting point of the drug and in a second pressure range to form a cooled dispersion of stabilized small particles containing the drug; and (e) drying the cooled dispersion to form dried small particles containing the poorly water-soluble drug.

However, in the method of Patent Document 1, preparation of an emulsion heated at a temperature higher than the melting point of the drug is essential, and there is a problem in maintaining the crystal form.

Patent Document 2 discloses effective solubilization or dispersion means of poorly soluble compounds by adding a combination of a predetermined amount of an oily component (fat), an emulsifier, and cyclodextrin. It teaches that a homomixer is used for coarse emulsification, and that a high-pressure homogenizer or an ultrasonic homogenizer is used for fine emulsification. However, in Patent Document 2, the composition containing a poorly soluble compound that is solubilized or dispersed takes the form of a fat emulsion, and not an aqueous suspension.

Patent Document 3 discloses a method for preparing a sterile freeze-dried formulation comprising the steps of:

(a) preparing sterile bulk aripiprazole having a desired particle size distribution;

(b) preparing a sterile vehicle for the sterile bulk aripiprazole;

(c) combining the sterile aripiprazole and the sterile vehicle to form a sterile primary suspension that includes a sterile mixture of solids;

(d) reducing the mean particle size of the sterile mixture of solids in the sterile primary suspension, e.g., by an aseptic wet milling to within the range from about 1 to about 100 μm, particularly about 1 to 10 μm, to form a sterile final suspension; and (e) freeze-drying the sterile final suspension to form the freeze-dried formulation.

It teaches that wet ball milling is preferred as the aseptic wet milling procedure in step (d).

Non-Patent Document 1 discloses that microfluidizers have two advantages over other methods of decreasing a mean particle size: the final products have no contaminants, and production is easily scaled up.

Patent Document 1: Japanese Unexamined Patent Publication No. 2003-531162
Patent Document 2: Japanese Unexamined Patent Publication No. 2005-22989
Patent Document 3: Japanese Unexamined Patent Publication No. 2007-509148
Patent Document 4: Japanese Unexamined Patent Publication No. 2007-509153
Patent Document 5: Japanese Patent No. 3760264
Patent Document 6: Japanese Patent No. 3750023
Non-Patent Document 1: Kathleen J. Illing, et al., "Use of Microfluidizer Processing for Preparation of Pharmaceutical Suspensions", Pharm. Tech., October 1996, pages 78 to 88.

Non-Patent Document 2: "Study on Crystal Transformation of Aripiprazole" Satoshi Aoki, et al., The Fourth Japan-Korea Symposium on Separation Technology (Oct. 6-8, 1996), p. 937-940

DISCLOSURE OF THE INVENTION

Problems to be Solved by the Invention

Suspensions prepared by suspending aripiprazole with a mean particle size of about 1 to about 10 μm in an aqueous vehicle are known to have excellent sustained-release properties. Wet ball milling of aripiprazole preferably having a mean particle size of about 100 μm or less, more preferably about 95% of the crystals having a particle size of 100 μm or less, is known as a process for producing such aripiprazole suspensions with a mean particle size of 1 to 10 μm, as shown in Patent Documents 3 and 4.

However, production of bulk aripiprazole having a mean particle size of about 100 μm or less required special methods, such as an impinging jet crystallization method, for producing a bulk drug. During the step of suspending the bulk aripiprazole having a mean particle size of about 100 μm or less in a vehicle, mixing under vacuum was necessary.

For this reason, a production method has been desired that can use bulk powder containing aripiprazole particles with a particle size of 100 μm or more in an amount of 10% or more, preferably bulk powder with a mean particle size of more than 100 μm, particularly about 110 μm to 1000 μm, more preferably 200 μm to 400 μm, produced by batch crystallization, without the need for vacuum mixing.

Moreover, the wet ball milling method has drawbacks: bead friction may possibly cause contamination, and ball mills capable of in-line sterilization are currently not commercially available. Therefore, a method that rarely induces contamination and uses a production apparatus capable of in-line sterilization has been desired.

Means for Solving the Problems

The present inventors found that even when using bulk aripiprazole containing 10% or more of aripiprazole particles with a particle size of 100 μm or more and having a mean particle size of 20 to 1000 μm, preferably bulk aripiprazole having a mean particle size of more than 100 μm, particularly preferably 110 μm to 1000 μm, most preferably 200 μm to 400 μm, the above problems can be solved by performing a first pulverization step using a high shear pulverizing machine such as a high shear homomixer, a dispersion machine that applies shear force to a material to be processed, a colloid mill, an ultrasonic dispersion machine, or a high-pressure jet type emulsifying dispersion machine such as a high-pressure homogenizer; and further performing a second pulverization step using a high-pressure jet type emulsifying dispersion machine such as a high-pressure homogenizer.

The present invention has been accomplished based on these findings and further research, and provides the following production method:

Item 1: A method for producing an aripiprazole suspension comprising the steps of:
(a) combining bulk aripiprazole and a vehicle to form a primary suspension;
(b) subjecting the primary suspension to first pulverization to form a secondary suspension; and
(c) subjecting the secondary suspension to second pulverization to form a final suspension.

Item 2: The method according to Item 1, wherein in the first pulverization of step (b), the secondary suspension is formed by pulverizing the primary suspension using a high shear pulverizing machine, a dispersion machine that applies shear force to a material to be processed, a colloid mill, an ultrasonic dispersion machine, or a high-pressure jet type emulsifying dispersion machine, and in the second pulverization of step (c), the final suspension is formed by pulverizing the secondary suspension using a high-pressure jet type emulsifying dispersion machine.

Item 3: The method according to Item 1 or 2, wherein in the first pulverization of step (b), the secondary suspension is formed by pulverizing the primary suspension using a high shear pulverizing machine or a dispersion machine that applies shear force to a material to be processed, and in the second pulverization of step (c), the final suspension is formed by pulverizing the secondary suspension using a high-pressure homogenizer.

Item 4: The method according to Item 3, wherein in step (c), the high-pressure homogenizer is used at a pulverization pressure of 300 to 1000 bar.

Item 5: The method according to Item 3 or 4, wherein in step (c), the high-pressure homogenizer is used at a pulverization pressure of 300 to 600 bar.

Item 6: The method according to any of Items 3 to 5, wherein in step (c), the high-pressure homogenizer is used at an inlet temperature of 1 to 70° C.

Item 7: The method according to Item 1 or 2, wherein in the first pulverization of step (b), the secondary suspension is formed by pulverizing the primary suspension using a high-pressure homogenizer, and in the second pulverization of step (c), the final suspension is formed by pulverizing the secondary suspension using a high-pressure homogenizer.

Item 8: The method according to Item 1, 2, or 7 wherein in the first pulverization of step (b), the secondary suspension is formed by pulverizing the primary suspension using the high-pressure homogenizer at a pulverization pressure of 50 to 200 bar, and in the second pulverization of step (c), the final suspension is formed by pulverizing the secondary suspension using a high-pressure homogenizer at a pulverization pressure of 200 to 1000 bar, wherein the difference between the pulverization pressure in step (b) and the pulverization pressure in (c) is 100 to 900 bar.

Item 9: The method according to Item 8, wherein in step (b), the pulverization pressure of the high-pressure homogenizer is in the range of 50 to 200 bar, and in step (c), the pulverization is carried out plural times and the pulverization pressure is raised stepwise within the range of 200 to 1000 bar.

Item 10: The method according to Item 9, wherein in step (c), the final pulverization pressure of the high-pressure homogenizer is 300 to 600 bar.

Item 11: The method according to any one of Items 7 to 10, wherein in steps (b) and (c), the high-pressure homogenizer is used at an inlet temperature of 1 to 50° C.

Item 12: The method according to any one of Items 1 to 11, wherein the vehicle contains at least one suspending agent selected from the group consisting of carboxymethyl cellulose, carboxymethyl cellulose salts, hydroxypropyl cellulose, hydroxypropylethyl cellulose, hydroxypropylmethyl cellulose and polyvinyl pyrrolidone.

Item 13: The method according to any one of Items 1 to 12, wherein the bulk aripiprazole contains 10% or more of aripiprazole particles with a particle size of 100 μm or more, and has a mean particle size of 20 μm to 1000 μm.

Item 14: The method according to any one of Items 1 to 13, wherein the bulk aripiprazole has a mean particle size of more than 100 μm.

Item 15: The method according to any one of Items 1 to 14, wherein the bulk aripiprazole has a mean particle size of 110 μm to 1000 μm.

Item 16: The method according to any one of Items 1 to 15, wherein the bulk aripiprazole has a mean particle size of 200 μm to 400 μm.

Item 17: The method according to any one of Items 1 to 16, wherein the aripiprazole in the aripiprazole suspension has a mean particle size of 1 to 10 μm.

Item 18: The method according to any one of Items 1 to 17, wherein the aripiprazole in the aripiprazole suspension has a mean particle size of 1 to 5 μm.

Item 19: The method according to any one of Items 1 to 18, wherein the aripiprazole in the aripiprazole suspension has a mean particle size of 2 to 4 μm.

Item 20: The method according to any one of Items 1 to 19, wherein the aripiprazole in the aripiprazole suspension has a mean particle size of 2 to 3 μm.

Item 21: The method according to any one of Items 1 to 6, comprising the steps of:
(I) combining sterile bulk aripiprazole with a mean particle size of 200 μm to 400 μm and a sterile vehicle (preferably a sterile vehicle containing carboxymethyl cellulose sodium salt) to form a sterile primary suspension;
(II) subjecting the sterile primary suspension to first pulverization using a high shear pulverizing machine or a dispersion machine that applies shear force to a material to be processed to form a sterile secondary suspension; and
(III) subjecting the sterile secondary suspension to second pulverization using a high-pressure homogenizer to form a sterile final suspension;
wherein the aripiprazole in the sterile final suspension (namely, the desired sterile aripiprazole suspension) has a mean particle size of 1 to 10 μm (preferably 1 to 5 μm, particularly 2 to 4 μm).

Item 22: The method according to any one of Items 1 to 21, wherein the bulk aripiprazole is in the form selected from the group consisting of monohydrate and Anhydride Crystals B.

Item 23: The method according to any one of Items 1 to 22, further comprising the step of filtering the final suspension with a filter having a nominal filtration rating of 10 to 225 μm.

Item 24: A method for producing a freeze-dried formulation of Aripiprazole Hydrate A, the method comprising the steps of: cooling the suspension produced by the method according to any one of Items 1 to 23 and containing Aripiprazole Hydrate A to −20 to −55° C. to freeze the suspension; and subsequently performing drying at a temperature lower than about 0° C.

Item 25: A method for producing a freeze-dried formulation containing aripiprazole in anhydrous form, the method comprising the following three steps of:
(1) cooling the aripiprazole suspension produced by the method according to any one of Items 1 to 23 using bulk aripiprazole in the form of a monohydrate or anhydrous crystals to −20 to −55° C. to freeze the suspension;
(2) performing primary drying at a temperature lower than about 0° C.; and
(3) performing secondary drying at a temperature higher than about 0° C.

Effect of the Invention

The present invention provides excellent effects as described below.

(a) The method for producing an aripiprazole suspension according to the present invention, which comprises two-step pulverization of bulk aripiprazole, is particularly effective when using bulk aripiprazole containing at least 10% of aripiprazole particles having a particle size of 100 μm or more and having a mean particle size of 20 μm to 1000 μm, preferably bulk aripiprazole having a mean particle size of more than 100 μm, particularly 110 μm to 1000 μm, most preferably 200 μm to 400 μm. However, regardless of the mean particle size, the method of the present invention readily produces an aripiprazole suspension having a mean particle size of 1 to 10 μm, preferably 1 to 5 μm, more preferably 2 to 4 μm, and most preferably 2 to 3 μm.

(b) By carrying out two-step pulverization, in accordance with the present invention, i.e., a first pulverization step using a high shear pulverizing machine (e.g., a high shear homomixer), a dispersion machine that applies shear force to a material to be processed, a colloid mill, an ultrasonic dispersion machine, or a high-pressure jet type dispersion machine (e.g., a high-pressure homogenizer), and a second pulverization step using a high-pressure jet type dispersion machine (e.g., a high-pressure homogenizer), an aripiprazole suspension having a mean particle size of 1 to 10 μm can be prepared, even using bulk powder with a large mean particle size, particularly bulk aripiprazole with a mean particle size of more than 100 μm obtained by batch crystallization, etc. Therefore, unlike Patent Document 4, special crystallization techniques like an impinging jet crystallization method are unnecessary for the preparation of bulk aripiprazole.

(c) The method of the invention uses, as sterile bulk aripiprazole, the bulk aripiprazole containing at least 10% of aripiprazole particles having a particle size of 100 μm or more and having a mean particle size of 20 μm to 1000 μm, preferably bulk aripiprazole having a mean particle size of more than 100 μm, particularly 110 μm to 1000 μm, and most preferably 200 μm to 400 μm, and therefore the step of combining bulk aripiprazole and a vehicle, the first pulverization step and the second pulverization step can be performed without adopting a vacuum mixing process as used in Patent Document 3. This eliminates the possibility of outside air mixing with the formulation during production of the sterile formulation, providing great advantages for a method for producing sterile products.

(d) Moreover, since no wear occurs as in a ball mill, there are no contamination problems caused by such wear.

(e) Short pass of large particles, which is a problem in wet ball milling, is less likely to occur, and therefore a homogeneous suspension free of coarse aripiprazole particles is obtained. As a result, the Aripiprazole suspension can be filtered with a smaller pore size for removing foreign substances after pulverization, and is advantageous from the standpoint of foreign substance control.

(f) In commercial scale aseptic production, clean-in-place (CIP) and sterilization-in-place (SIP) are difficult with respect to apparatuses such as ball mills; however, the production apparatus used in the pulverization method (first pulverization step and second pulverization step) of the invention allows for CIP and SIP. Hence, the apparatus is easily kept sterile by in-line sterilization.

(g) When carboxymethyl cellulose or a salt thereof is selected as a suspending agent for a vehicle in the present production method, it is possible to avoid excessive pulverization in which the mean particle size falls below 1 μm.

BEST MODE FOR CARRYING OUT THE INVENTION

The production method of the present invention is described in detail below.

In the present invention, the term "mean particle size" refers to volume mean diameter as measured by laser-light scattering (LLS) methods. Particle size distribution is measured by LLS methods, and mean particle size is calculated from the particle size distribution.

Bulk Aripiprazole

Aripiprazole has the structure

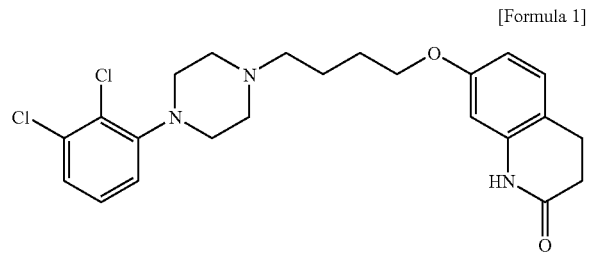 [SMILES: O=C1CCc2ccc(OCCCCN3CCN(c4cccc(Cl)c4Cl)CC3)cc2N1]

[Formula 1]

and is an atypical antipsychotic agent useful in treating schizophrenia. It has poor aqueous solubility (<1 μg/ml at room temperature).

Aripiprazole bulk drug or bulk powder may have any mean particle size and particle size distribution. Generally, it is preferable to use bulk aripiprazole containing aripiprazole particles having a particle size of 100 μm or more in a proportion of at least 10% and having a mean particle size of 20 μm to 1000 μm, preferably bulk aripiprazole having a mean particle size of more than 100 μm, particularly 110 μm to 1000 μm, and most preferably 200 μm to 400 μm.

Moreover, the crystal form of bulk aripiprazole is not limited and various forms are usable. Examples of the crystal forms of aripiprazole include monohydrate disclosed in Non-Patent Document 2 (in the present specification, the term "a monohydrate" as such means the monohydrate disclosed in Non-Patent Document 2), Hydrate A and Anhydride Crystals B that are disclosed in Patent Document 5, Anhydride Crystals C, Anhydride Crystals D, Anhydride Crystals E, Anhydride Crystals F, and Anhydride Crystals G that are disclosed in Patent Document 6. Among these, a monohydrate and Anhydride Crystals B are preferable.

In the present invention, by using a monohydrate crystal (Non-Patent Document 2) as bulk aripiprazole, a suspension of Hydrate A (Patent Document 5) is obtained by the method of the invention. Also, by using Hydrate A as bulk aripiprazole, a suspension of Hydrate A can be obtained by the method of the invention. Anhydride Crystals B (Patent Document 5), Anhydride Crystals C, Anhydride Crystals D, Anhydride Crystals E, Anhydride Crystals F, and Anhydride Crystals G (Patent Document 6) can also be used as bulk aripiprazole. With these crystals, an aripiprazole suspension in which Hydrate A and anhydrous aripiprazole are mixed is obtained. Additionally, Anhydride Crystals B, Anhydride Crystals C, Anhydride Crystals D, Anhydride Crystals E, Anhydride Crystals F, or Anhydride Crystals G may be recrystallized from ethanol and water, or the like in advance to thereby prepare a monohydrate, and the resulting monohydrate may be used as bulk Aripiprazole.

Vehicle

The vehicle used in the invention generally includes:

(1) one or more suspending agents, (2) water for injection, (3) optionally one or more bulking agents or isotonic agents, (4) optionally one or more buffers, and (5) optionally one or more pH adjusting agents.

The suspending agent will be present in an amount within the range from about 0.2 to about 10% by weight, preferably about 0.3 to about 5% by weight, more preferably about 0.4 to about 0.9% by weight, based on the total weight of the sterile injectable formulation (the aripiprazole suspension of the invention). Examples of suspending agents suitable for use include, but are not limited to, one, two or more of the following: carboxymethyl cellulose or a salt thereof (e.g., sodium carboxymethyl cellulose), hydroxypropyl cellulose, hydroxypropylethyl cellulose, hydroxypropylmethyl cellulose, and polyvinylpyrrolidone, with carboxymethyl cellulose or a salt thereof, particularly sodium salt, being preferred. Other suspending agents suitable for use in the vehicle for the aripiprazole include various polymers, low molecular weight oligomers, natural products, and surfactants, including nonionic and ionic surfactants, such as cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens (registered trademark); e.g., Tween 20 (registered trademark) and Tween 80 (registered trademark) (ICI Specialty Chemicals)); polyethylene glycols (e.g., Carbowaxs 3350 (registered trademark) and 1450 (registered trademark), and Carbopol 934 (registered trademark) (Union Carbide)), dodecyl trimethyl ammonium bromide, polyoxyethylene stearates, colloidal silicon dioxide, phosphates, sodium dodecyl sulfate, carboxymethylcellulose calcium, hydroxypropyl celluloses (e.g., HPC, HPC-SL, and HPC-L), methylcellulose, hydroxyethylcellulose, hydroxypropylmethylcellulose, hydroxypropylmethyl-cellulose phthalate, non-crystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68 (registered trademark) and F108 (registered trademark), which are block copolymers of ethylene oxide and propylene oxide); poloxamines (e.g., Tetronic 908 (registered trademark), also known as Poloxamine 908 (registered trademark), which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phosphatidyl glycerol, dioctylsulfosuccinate (DOSS); Tetronic 1508 (registered trademark) (T-1508) (BASF Wyandotte Corporation), dialkylesters of sodium sulfosuccinic acid (e.g., Aerosol OT (registered trademark), which is a dioctyl ester of sodium sulfosuccinic acid (American Cyanamid)); Duponol P (registered trademark), which is a sodium lauryl sulfate (DuPont); Tritons X-200 (registered trademark), which is an alkyl aryl polyether sulfonate (Rohm and Haas); Crodestas F-110 (registered trademark), which is a mixture of sucrose stearate and sucrose distearate (Croda Inc.); p-isononylphenoxypoly-(glycidol), also known as Olin-10G (registered trademark) or Surfactant 10-G (registered trademark) (Olin Chemicals, Stamford, Conn.); Crodestas SL-40 (Croda, Inc.); and SA9OHCO, which is $C_{18}H_{37}CH_2(CON(CH_3))$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside;

n-hexyl β-D-glucopyranoside; nonanoyl-N-methylglucamide; n-nonyl β-D-glucopyranoside; octanoyl-N-methylglucamide; n-octyl-β-D-glucopyranoside; octyl β-D-thioglucopyranoside; and the like.

Most of these suspending agents are known pharmaceutical excipients, and are described in detail in the Handbook of Pharmaceutical Excipients, published jointly by the American Pharmaceutical Association and The Pharmaceutical Society of Great Britain (The Pharmaceutical Press, 1986), specifically incorporated by reference. The suspending agents are commercially available and/or can be prepared by techniques known in the art.

In the invention, it is preferable to use carboxymethyl cellulose or a salt thereof, hydroxypropyl cellulose, hydroxypropylethyl cellulose, hydroxypropylmethyl cellulose, or polyvinylpyrrolidone as a suspending agent for a vehicle. The use of carboxymethyl cellulose (hereinafter occasionally referred to as "CMC") or a salt thereof (preferably sodium salt (hereinafter occasionally referred to as "CMCNa")) particularly ensures the prevention of excessive pulverization in which the mean particle size falls below 1 μm, even when pulverization in the second pulverization step is repeatedly performed or performed over a prolonged period.

The viscosity range of carboxymethyl cellulose or the sodium salt thereof may be suitably selected from a wide range. Generally, the viscosity of a 4% aqueous solution at 25° C. is preferably about 20 to 400 cps, particularly about 50 to 200 cps.

If desired, the vehicle of the present invention may contain bulking agent (also referred to as a cryogenic/lyophilize protecting agent) or isotonic agent. The agent will be present in an amount within the range from about 1 to about 10% by weight, preferably from about 1.5 to about 8% by weight, more preferably from about 2 to about 5% by weight, based on the total weight of the sterile injectable formulation (the aripiprazole suspension of the invention). Examples of bulking agents or isotonic agents suitable for use herein include, but are not limited to, one, two or more of the following: mannitol, sucrose, maltose, xylitol, glucose, starches, sorbitol, and the like, with mannitol being preferred for formulations where the mean particle size is about 1 micron or above.

As required, the vehicle of the present invention may contain buffer. The buffer will be employed in an amount to adjust the pH of an aqueous suspension of aripiprazole to from about 6 to about 8, preferably about 7. To achieve such a pH, the buffer, depending on the type, will usually be employed in an amount within the range from about 0.02 to about 2% by weight, preferably from about 0.03 to about 0.1% by weight, based on the total weight of the sterile injectable formulation (the aripiprazole suspension of the invention). Examples of buffers suitable for use herein include, but are not limited to, one, two or more of the following: sodium phosphate, potassium phosphate, or TRIS buffer, with sodium phosphate being preferred.

The vehicle of the invention may optionally include a pH adjusting agent that is employed in an amount to adjust the pH of the aqueous suspension of aripiprazole within the range from about 6 to about 7.5, preferably about 7, and may be an acid or base depending upon whether the pH of the aqueous suspension of the freeze-dried aripiprazole needs to be raised or lowered to reach the desired neutral pH of about 7. Thus, when the pH needs to be lowered, an acidic pH adjusting agent such as hydrochloric acid or acetic acid, preferably hydrochloric acid, may be employed. When the pH needs to be raised, a basic pH adjusting agent such as sodium hydroxide, potassium hydroxide, magnesium oxide or magnesium hydroxide, preferably sodium hydroxide, will be employed.

Production Method of the Invention

The production method of the invention is described below.

As described above, the present invention provides a method for producing an aripiprazole suspension, the method comprising the steps of:

(a) combining bulk aripiprazole and a vehicle to form a primary suspension;

(b) subjecting the primary suspension to first pulverization to form a secondary suspension; and (c) subjecting the secondary suspension to second pulverization to form a final suspension.

According to one preferred embodiment of the invention, there is provided the following method: A method for producing a sterile aripiprazole suspension in which aripiprazole has a mean particle size of 1 to 10 μm, preferably 1 to 5 μm, more preferably 2 to 4 μm, most preferably about 2 to 3 μm, the method comprising the steps of:

(A) combining sterile bulk aripiprazole and a sterile vehicle to form a sterile primary suspension;

(B) subjecting the sterile primary suspension to first pulverization using a high shear pulverizing machine, a dispersion machine that applies shear force to a material to be processed, a colloid mill, an ultrasonic dispersion machine, or a high-pressure jet type emulsifying dispersion machine, to form a sterile secondary suspension; and (C) subjecting the sterile secondary suspension to second pulverization using a high-pressure jet type emulsifying dispersion machine to form a sterile final suspension.

In carrying out the method for preparing the sterile aripiprazole suspension of the invention, it is required that everything be sterile so that sterile aripiprazole and a sterile vehicle are combined aseptically to form a sterile suspension.

However, when it is possible to perform sterilization after the desired aripiprazole suspension is obtained, the sterile aripiprazole and the sterile vehicle need not necessarily be used in the method including steps (A), (B) and (C) above.
(A) Step of Combining Sterile Bulk Aripiprazole and Sterile Vehicle to Form a Sterile Primary Suspension This step (A) comprises the following steps (A-1), (A-2) and (A-3).
(A-1) Step of Preparing Sterile Bulk Aripiprazole This step typically prepares sterile bulk aripiprazole containing 10% or more of aripiprazole particles having a particle size of 100 μm or more and having a mean particle size of 20 μm to 1000 μm, preferably sterile bulk aripiprazole having a mean particle size of more than 100 μm, particularly preferably 110 μm to 1000 μm, most preferably 200 μm to 400 μm.

The method for sterilizing bulk aripiprazole is not limited, and can be selected from a number of methods including aseptic crystallization, autoclave sterilization, gas sterilization, and radiation sterilization. Among them, aseptic crystallization is preferred.

Aseptic crystallization is a process in which a solution prepared by dissolving aripiprazole in a solvent is sterilized by filtration sterilization etc., and then crystallization is carried out. A number of such processes, such as a continuous crystallization method or a batch crystallization method, can be used without limitation.

Autoclave sterilization, gas sterilization, or radiation sterilization may be conducted in accordance with conventional methods that can sterilize aripiprazole.

The crystalline form of sterile aripiprazole is known to exist in the form of monohydrate, Hydrate A, Anhydride Crystals B, Anhydride Crystals C, Anhydride Crystals D, Anhydride Crystals E, Anhydride Crystals F, and Anhydride Crystals G, etc., all of which may be employed in the formulation of the present invention. Among these, monohydrate and Anhydride Crystals B are most preferable.

(A-2) Step of Preparing a Sterile Vehicle for the Sterile Bulk Aripiprazole

A vehicle for the sterile bulk aripiprazole is prepared by uniformly dissolving the above-mentioned suspending agent, and optionally a bulking agent or an isotonic agent, a buffer, and a pH adjusting agent in water for injection, and sterilizing the resulting vehicle solution.

The method for sterilizing the vehicle solution is not limited, but is preferably filtration with a filter. The pore size of the filter is preferably about 0.2 µm.

(A-3) Step of Combining the Sterile Aripiprazole and the Sterile Vehicle to Form a Sterile Primary Suspension The sterile bulk aripiprazole and the sterile vehicle are aseptically mixed to form a sterile primary suspension. The aseptic mixing process is not limited as long as it is a known aseptic stirring technique, such as an aseptic mixing method using a mechanical stirring device with a propeller. Conditions at the time of mixing are not limited. For example, preferable stirring conditions are such that powder particles are mixed in a vehicle without foaming.

The concentration of the sterile bulk aripiprazole to be dispersed in the sterile vehicle may be suitably selected from a wide range, but generally is about 10 to 400 mg/ml, preferably 50 to 250 mg/ml, most preferably about 100 mg/ml.

The mixing procedure in step (A-3) may be performed under ordinary pressure (atmospheric pressure) or increased pressure. Unlike in Patent Document 3, there is no need to adopt vacuum or reduced pressure conditions. Under increased pressure, generally, the mixing procedure is preferably carried out at a gauge pressure of about 0 to 0.3 MPa. Preferred temperature conditions in step (A-3) is about 5 to 80° C., particularly about 10 to 40° C. Unlike in Patent Document 1, there is no need to employ temperatures at or above the melting point of bulk aripiprazole.

(B) Step of Subjecting the Sterile Primary Suspension to First Pulverization Using a High Shear Pulverizing Machine (e.g., High Shear Homomixer), a Dispersion Machine that Applies Shear Force to a Material to be Processed, a Colloid Mill, an Ultrasonic Dispersion Machine, or a High-Pressure Jet Type Emulsifying Dispersion Machine (e.g., High-Pressure Homogenizer) to Form a Sterile Secondary Suspension The particle size of the aripiprazole is reduced to a desired level by a first pulverization step. Examples of pulverizing machines used in the first pulverization step include those which can suitably produce particles having a target particle size, such as a high shear pulverizing machine, a dispersion machine that applies shear force to a material to be processed, a colloid mill, an ultrasonic dispersion machine (pulverizing machine), or a high-pressure jet type emulsifying dispersion machine (e.g., high-pressure homogenizer). A high shear pulverizing machine or a dispersion machine that applies shear force to a material to be processed, are preferably used. As such high shear pulverizing machines, e.g., a high shear homomixer, various commercial products are available, such as "Clearmix" (trade name, produced by M-Technique Co., Ltd.). However, they are not limited as long as they are high shear pulverizing machines that are air-tight and free of foaming.

Conditions under which pulverization is carried out using a high shear homomixer may be such that a target particle size can be suitably obtained. The target particle size may be such that the flow path of a homogenizer used in the subsequent second pulverization step is not clogged. Typical conditions may be such that the mean particle size is reduced to about 5 to 100 µm, preferably 5 to 50 µm.

In the first pulverization step, pulverization is preferably carried out using the above-mentioned apparatus at a rotating blade (rotor) circumferential speed of typically 5 to 50 m/s, preferably 10 to 40 m/s, and more preferably about 15 to 35 m/s. It is particularly effective to operate a high shear pulverizing machine, such as a high shear homomixer (e.g., those available under the trade name of Clearmix), at such a circumferential speed. For example, secondary suspensions with a mean particle size of 10 to 20 µm were obtained from a primary suspension (4 L, laboratory scale) subjected to a first pulverization using a Clearmix CLM-1.5S at a circumferential speed of 28.3 m/s, as well as from primary suspensions (40 L, scale-up) subjected to a first pulverization using a Clearmix CLM-9S or Clearmix CLM-15S at a circumferential speed of 28.3 m/s.

Temperature conditions in step (B) are about 5 to 80° C., particularly about 10 to 40° C.

In place of the high shear homomixer, a dispersion machine that applies shear force to a material to be dispersed, namely, a dispersion apparatus that exerts shear force to aripiprazole particles during processing, can be used. Various commercial products are available as such dispersion machines, including a dispersion machine that applies shear force to a material to be processed (trade name: "T-50 Basic" produced by IKA Japan, Inc.). Conditions for pulverization by these dispersion machines may be such that a target particle size can be suitably obtained. The target particle size may be such that the flow path of a homogenizer used in the subsequent second pulverization step is not clogged. Typical conditions may be such that the mean particle size is reduced to about 5 to 100 µm, preferably 5 to 50 µm.

Colloid mills, ultrasonic dispersion machine (pulverizing machine) or high-pressure jet type emulsifying dispersion machines may also be used under substantially the same conditions as mentioned above.

The pulverization in step (B) may be conducted under ordinary pressure (atmospheric pressure) or increased pressure. Unlike in Patent Document 3, there is no need to adopt vacuum or reduced pressure conditions. Under increased pressure, generally, the mixing procedure is preferably carried out at a gauge pressure of about 0 to 0.3 MPa.

(C) Step of Subjecting the Sterile Secondary Suspension to Second Pulverization Using a High-Pressure Jet Type Emulsifying Dispersion Machine (e.g., High-Pressure Homogenizer) to Form a Sterile Final Suspension The particle size of the aripiprazole is reduced to a desired level by a second pulverization step. Examples of pulverizing machines used in the second pulverization step include a high-pressure jet type emulsifying dispersion machine that treats process liquids under high pressure. A preferred high-pressure jet type emulsifying dispersion machine is a high-pressure homogenizer in which pump-pressurized process liquid is ejected as a jet-stream at high pressure by adjusting a specially designed valve in an ejecting section. Typical models of this type include EmulsiFlex (produced by Avestin) and high-pressure homogenizers produced by APV, NIRO SOAVI, or Sanwa Machine Co., Inc. Other dispersion machines can also be used in which process liquids are passed at high pressure through orifices of various shapes arranged in such a direction that the process liquids collide with each other. Typical models of this type include Microfluidizer (produced by Microfluidics), Starburst (Sugino Machine Ltd.), and Nanomizer (Yoshida Kikai Co., Ltd.), etc.

The pulverization pressure of the high-pressure homogenizer is preferably about 300 to 1000 bar, more preferably about 300 to 600 bar. The inlet temperature of the high-pressure homogenizer may be suitably selected from a wide range, but is generally about 1 to 70° C., preferably about 5 to 40° C.

By carrying out the second pulverization step under the above conditions, the mean particle size of the aripiprazole in the final suspension is preferably adjusted to about 1 to 10 µm, preferably 1 to 5 µm, more preferably 2 to 4 µm, most preferably 2 to 3 µm. The aripiprazole suspension having a mean particle size of 2 to 3 µm is useful because it has an excellent absorption profile and undergoes no sedimentation during manufacturing process.

The second pulverization step of step (C) may be carried out by passing the suspension through a high-pressure homogenizer plural times. In such a case, discrete-pass method and recirculation method may be employed, giving similar results (see Examples 1-5 and Example 6 described later). Both systems may also be combined (see Example 7, described later).

The discrete-pass method specifically refers to a method in which a suspension is processed by passing portions of the suspension through, for example, a high-pressure homogenizer until all portions thereof are processed while recovering the processed suspension. When the suspension is processed plural times by discrete-pass method, the recovered suspension is processed by passing portions of the recovered suspension through a high-pressure homogenizer until all portions thereof are processed while recovering the processed suspension, and this procedure is repeated.

The recirculation method specifically refers to a method in which a tank or vessel containing a suspension, connected to the inlet of, e.g., a high-pressure homogenizer, is also connected to the outlet of the homogenizer via a recycle line, and the suspension in the tank or vessel is continuously processed by the homogenizer, without being recovered, so that the processed suspension is recycled through the recycle line to the tank or vessel where it is mixed with unprocessed suspension, and the mixture is continuously passed through the homogenizer, and thus the suspension is processed with recirculation.

The pulverization in step (C) does not require vacuum or reduced pressure conditions, unlike in Patent Document 3.

When a high-pressure homogenizer is used in both the first and second pulverization steps, steps (B) and (C) of the production method comprising the above-mentioned steps (A) to (C) of the invention are preferably carried out as shown in the following steps (BB) and (CC), respectively.

Step (BB)

Step (BB) of the invention is a first pulverization step in which the sterile primary suspension obtained in step (A) is pulverized using a high-pressure homogenizer at a pulverization pressure of 50 to 200 bar, preferably 70 to 150 bar, to obtain a secondary suspension. It was found that this step, when adopted, solves the clogging problem mentioned above.

In other words, the use of the high-pressure homogenizer at a pulverization pressure within the range of 50 to 200 bar, preferably 70 to 150 bar, prevents the clogging of the flow path of the high-pressure homogenizer.

The inlet temperature of the high-pressure homogenizer may be suitably selected from a wide range, but generally is about 1 to 50° C., preferably about 5 to 40° C.

A sterile secondary suspension is obtained in this manner.

Step (CC)

Step (CC) of the invention is a second pulverization step in which the sterile secondary suspension obtained in step (BB) is pulverized using a high-pressure homogenizer at a pulverization pressure of 200 to 1000 bar to obtain a sterile final suspension. This step provides an aripiprazole suspension having the desired mean particle size of 1 to 10 µm, preferably 1 to 5 µm, more preferably 2 to 4 µm, most preferably about 2.5 µm.

In step (CC), the pulverization pressure of the high-pressure homogenizer needs to be increased, compared with the pulverization pressure in step (BB). Generally, the pulverization pressure in step (CC) is preferably set higher than that of step (BB) by about 100 to 900 bar, particularly about 200 to 500 bar.

Preferred pulverization pressure of the high-pressure homogenizer in step (CC) is 200 to 1000 bar, particularly about 300 to 600 bar.

Also, when the pulverization is carried out plural times in step (CC), the pulverization pressure can be increased stepwise within the range of 200 to 1000 bar. In this case, the final pressure is preferably about 300 to 1000 bar, more preferably about 300 to 600 bar.

The inlet temperature of the high-pressure homogenizer is suitably selected from a wide range, but is generally about 1 to 50° C., preferably about 5 to 40° C.

The second pulverization step of step (CC) may be carried out by passing the suspension through a high-pressure homogenizer plural times. The discrete-pass method and a recirculation method mentioned above may be employed, giving similar results. Both methods may also be combined.

The pulverization in step (CC) does not require vacuum or reduced pressure conditions, unlike in Patent Document 3.

In the invention, it is possible to perform cleaning and sterilization of the surfaces that are exposed to liquids, of the machines used in the invention, such as a high shear pulverizing machine, a dispersion machine that applies shear force to a material to be processed, a colloid mill, an ultrasonic dispersion machine, and a high-pressure jet type emulsifying dispersion machine, by conducting clean-in-place (CIP) and sterilization-in-place (SIP). In-line sterilization is also possible. CIP may be carried out using water, hot water, alkaline water, acidic water, or organic solvent, with optional addition of one or more cleaning agents conventionally used, such as alkaline detergents, neutral detergents and acidic detergents. SIP may be carried out using pure steam, high pressure high temperature water, etc.

Thus, a sterile aripiprazole suspension wherein the aripiprazole has a mean particle size of 1 to 10 µm is obtained by aseptically pulverizing, in step (b), a sterile primary aripiprazole suspension produced in step (a) using a high shear pulverizing machine (such as a high-shear homomixer), a dispersion machine that applies shear force to a material to be processed, a colloid mill, an ultrasonic dispersion machine, or a high-pressure jet type emulsifying dispersion machine (such as a high-pressure homogenizer), whose surfaces exposed to liquids have been sterilized, to form a sterile secondary suspension, and aseptically pulverizing the resulting sterile secondary suspension in step (c) using a high-pressure jet type emulsifying dispersion machine (such as a high-pressure homogenizer), whose surfaces exposed to liquids have been sterilized.

Aripiprazole Aqueous Suspension

The aripiprazole in the aripiprazole aqueous suspension produced by the production method of the invention has a mean particle size of 1 to 10 μm, preferably 1 to 5 μm, more preferably 2 to 4 μm, most preferably about 2 to 3 μm.

According to the production method of the invention, no matter how large the mean particle size of bulk aripiprazole is, the mean particle size of aripiprazole in the suspension finally obtained is controlled within the above range. Therefore, the method has great advantages: there are few restrictions in the production of sterile bulk poweder; when using bulk powder with a large particle size, air bubble entrainment rarely occurs during preparation of the suspension, and the defoaming process is easy; there is no need for reduced pressure, and the possibility of contamination from outside air is significantly decreased.

According to the production method of the invention, a homogeneous final suspension free of coarse aripiprazole particles can be produced, and therefore, the final suspension obtained (namely, the desired aripiprazole suspension) may be filtered for removing foreign substances, if so desired. The filter to be used has a pore size such that the filter has a nominal filtration rating of 10 to 225 μm, preferably 20 to 70 μm. Therefore, the production method of the invention may further comprise the step of filtering the final suspension obtained in step (c) with a filter having a nominal filtration rating of 10 to 225 μm.

The resulting final suspension (namely, the desired aripiprazole suspension) preferably has an aripiprazole concentration of about 10 to 400 mg/ml, more preferably about 50 to 250 mg/ml, most preferably 100 mg/ml.

The sterile aripiprazole suspension obtained by the production method of the invention is administered, for example, intramuscularly and subcutaneously, as formulation for injection.

Method for Producing Freeze-Dried Formulation

The sterile aripiprazole suspension obtained by the aforementioned method may be freeze-dried to produce a freeze-dried formulation.

More specifically, the final aripiprazole suspension may be freeze-dried into a freeze-dried formulation of a desired polymorphic form (an anhydrate, Hydrate A, or a mixture of them). To obtain a freeze-dried formulation of Aripiprazole Hydrate A, a monohydrate or Hydrate A is used as bulk aripiprazole, and the Hydrate A suspension obtained by the method of the invention is subjected to the following freeze-drying cycle.

The freeze-drying cycle comprises cooling the suspension to −20° C. to −55° C. at a suitable cooling rate to freeze the suspension, and performing a drying step at a temperature below around 0° C. (preferably around 0° C. to −15° C.) under a suitable vacuum (e.g. about 1 to 100 Pa) and for a suitable duration (e.g. until the freeze-dried formulation is obtained; typically for about 10 to 100 hours).

If a freeze-dried formulation containing aripiprazole in anhydrous form is desired, aripiprazole in the form of a monohydrate or anhydrous crystals is used as the bulk aripiprazole, and the suspension obtained by the method of the invention is subjected to the following freeze-drying cycle. The freeze-drying cycle comprises the three steps (freezing, primary drying, secondary drying). Specifically, the freeze-drying cycle comprises cooling the suspension to −20° C. to −55° C. at a suitable cooling rate to freeze the suspension; performing primary drying at a temperature below around 0° C. (preferably around 0° C. to −20° C.) under a suitable vacuum (e.g. about 1 to 100 Pa) and for a suitable duration (typically for about 10 to 100 hours); and performing secondary drying at a temperature above around 0° C. (preferably 0° C. to 60° C.) under a suitable vacuum (e.g. about 0.1 to 20 Pa) and for a suitable duration (e.g. until the freeze-dried formulation is obtained; typically for about 10 to 100 hours).

The freeze-dried formulation thus produced can be easily reconstituted into a desired aripiprazole suspension using water for injection immediately before the administration. Therefore, the freeze-dried formulation is useful as a formulation immediately prepared before use. Even by a reconstitution method as simple as adding water for injection to the formulation and shaking the mixture by hand, a homogeneous aripiprazole suspension can be obtained.

EXAMPLES

Examples are provided below to describe the present invention in further detail.

In each example, the mean particle size is the volume mean diameter measured with a laser-light scattering (LLS) diffraction particle size analyzer (laser diffraction particle size analyzer SALD-3000J, Shimadzu Corp.). The terms "10% diameter", "50% diameter", and "90% diameter" refer to, in particle size distribution, the particle diameter of the point where the distribution curve of integration (%) intersects with 10% value of the integrated value, the particle diameter of the point at the intersection with 50% value, and the particle diameter of the point at the intersection with 90% value, respectively. Measurement conditions are as follows. Medium: water; refractive index: 2.00 to 0.20i; cell: flow cell.

In each example, both steps of preparing a vehicle and combining bulk aripiprazole and the vehicle to form a primary suspension were carried out at room temperature (20 to 30° C.), unless otherwise specified. The first pulverization step for pulverizing the primary suspension was carried out at 20 to 45° C., unless otherwise specified.

The high-pressure homogenizer used in each example is a commercially available high-pressure homogenizer (trade name "PANDA 2K Type", manufactured by NIRO SOAVI).

Example 1

(a) Sodium carboxymethyl cellulose (18.30 g), 91.52 g of mannitol, and 1.63 g of sodium dihydrogen phosphate monohydrate were dissolved in purified water. The total weight was 2059.2 g. The solution was adjusted to pH 7.0 with a 1 mol/L sodium hydroxide aqueous solution, and filtered through a 0.2 μm filter.

In the resulting filtrate (1872 g), bulk aripiprazole monohydrate produced by batch crystallization (208 g; mean particle size of the bulk powder=258 μm; 10% diameter=99 μm; 50% diameter=280 μm; 90% diameter=609 μm) was dispersed to form a primary suspension.

The dispersion procedure for preparing the primary suspension was conducted by using a Three-One Motor (produced by HEIDON) for stirring with 100 mm-diameter blades at about 200 to 400 rpm. (The same applies to the following examples, unless otherwise noted.)

(b) The primary suspension was pulverized with a high shear homomixer (trade name: "Clearmix (CLM-1.5S)", produced by M Technique Co., Ltd.) at 18000 rpm for 7.5 minutes per liter. As a result, a secondary suspension was obtained.

(c) The obtained secondary suspension was cooled or warmed so as to keep the inlet temperature at about 10° C., about 20° C., about 40° C., and about 60° C. The suspension was pulverized by passing 10 times through a high-pressure homogenizer at 600 bar by discrete-pass method.

The mean particle size of the suspensions pulverized once and pulverized 10 times was measured with a particle size distribution analyzer (SALD-3000J, Shimadzu Corp.). The results are shown below.

TABLE 1

| Number of Times | Mean Particle Size (μm) | | | |
|---|---|---|---|---|
| Pulverized | 10° C. | 20° C. | 40° C. | 60° C. |
| 1 | 5.1 | 5.0 | 4.5 | 4.9 |
| 10 | 1.8 | 1.9 | 2.3 | 3.9 |

Table 1 reveals the following:

(i) Even when bulk aripiprazole monohydrate produced by batch crystallization was used, passing the suspension once through a high-pressure homogenizer at 600 bar at an inlet temperature of 10 to 60° C. in the second pulverization (step (c)) permitted the preparation of an aripiprazole suspension with a mean particle size of 1 to 10 μm.

(ii) Passing the suspension 10 times through a high-pressure homogenizer at 600 bar at an inlet temperature of 10 to 60° C. in the second pulverization (step (c)) enabled the preparation of an aripiprazole suspension with a mean particle size of about 2 to 4 μm.

(iii) Passing the suspension 10 times through a high-pressure homogenizer at 600 bar at an inlet temperature of 10 to 40° C. in the second pulverization (step (c)) allowed the preparation of an aripiprazole suspension with a mean particle size of about 2 to 3 μm.

This shows that a suspension with the desired mean particle size (1-10 μm, preferably 1-5 μm, more preferably 2 to 4 μm) is obtained even by the use of bulk powder with a large mean particle size, which is one of the effects of the present invention.

The same results as above are obtained even using sterile bulk aripiprazole and a sterile vehicle. The same applies to the following examples.

Example 2

Sodium carboxymethyl cellulose (45.76 g), 228.80 g of mannitol, and 4.07 g of sodium dihydrogen phosphate monohydrate were dissolved in purified water. The total weight was 5148 g. The solution was adjusted to pH 7.0 with a 1 mol/L sodium hydroxide aqueous solution, and filtered through a 0.2 μm filter.

In the resulting filtrate (1872 g), bulk aripiprazole monohydrate produced by batch crystallization (208 g; mean particle size of the bulk powder=239 μm; 10% diameter=99 μm; 50% diameter=276 μm; 90% diameter=632 μm) was dispersed to form a primary suspension.

The primary suspension was pulverized with Clearmix (CLM-1.5S) at 18000 rpm for 7.5 minutes per liter. As a result, a secondary suspension was obtained.

The obtained secondary suspension was cooled so as to keep the inlet temperature at about 20° C., and pulverized by passing 10 times through a high-pressure homogenizer at 300 bar, 600 bar, and 1000 bar by discrete-pass method. The mean particle size of the suspensions pulverized once and pulverized 10 times was measured with a particle size distribution analyzer (SALD-3000J, Shimadzu Corp.). The results are shown below.

TABLE 2

| Number of Times | Mean Particle Size (μm) | | |
|---|---|---|---|
| Pulverized | 300 bar | 600 bar | 1000 bar |
| 1 | 5.7 | 4.5 | 4.3 |
| 10 | 2.6 | 1.9 | 2.5 |

Table 2 indicates the following:

(i) Even when bulk aripiprazole monohydrate produced by batch crystallization was used, passing the suspension once though a high-pressure homogenizer at 300 to 1000 bar enabled the preparation of an aripiprazole suspension with a mean particle size of 1 to 10 μm.

(ii) Passing the suspension 10 times though a high-pressure homogenizer at 300 to 1000 bar allowed the preparation of an aripiprazole suspension with a mean particle size of 2 to 3 μm.

(iii) The preparation of an aripiprazole suspension with a mean particle size of 2 to 3 μm is also possible at 1000 bar. However, the desired aripiprazole suspension can be efficiently obtained at 300 to 600 bar.

Example 3

Sodium carboxymethyl cellulose (45.76 g), 228.80 g of mannitol, and 4.07 g of sodium dihydrogen phosphate monohydrate were dissolved in purified water. The total weight was 5148 g. The solution was adjusted to pH 7.0 with a 1 mol/L sodium hydroxide solution and filtered through a 0.2 μm filter. Two kinds of sodium carboxymethyl cellulose with a viscosity of 93 cps (4% aqueous solution, 25° C.) and 187 cps (4% aqueous solution, 25° C.) were used.

In the resulting filtrate (1872 g), bulk aripiprazole monohydrate produced by batch crystallization (208 g; mean particle size of the bulk powder used for studying sodium carboxymethyl cellulose with a viscosity of 93 cps=258 μm; 10% diameter=99 μm; 50% diameter=280 μm; 90% diameter=609 μm; mean particle size of the bulk powder used for studying sodium carboxymethyl cellulose with a viscosity of 187 cps=239 μm; 10% diameter=99 μm; 50% diameter=276 μm; 90% diameter=632 μm) was dispersed to form primary suspensions.

Each of the primary suspensions was pulverized with Clearmix (CLM-1.5S) at 18000 rpm for 7.5 minutes per liter. As a result, secondary suspensions were obtained.

The obtained secondary suspensions were cooled so as to keep the inlet temperature at about 20° C., and pulverized by passing 10 times through a high-pressure homogenizer at 600 bar by discrete-pass method. The mean particle size of the suspensions pulverized once and pulverized 10 times was measured with a particle size distribution analyzer (SALD-3000J, Shimadzu Corp.). The results are shown below.

TABLE 3

| Number of Times | Mean Particle Size (μm) Viscosity of Sodium Carboxymethyl Cellulose | |
|---|---|---|
| Pulverized | 93 cps | 187 cps |
| 1 | 5.0 | 4.5 |
| 10 | 1.9 | 1.9 |

Table 3 indicates that the difference in viscosity of CMCNa does not influence the pulverization.

Example 4

Sodium carboxymethyl cellulose (33.28 g), 166.40 g of mannitol, and 2.96 g of sodium dihydrogen phosphate monohydrate were dissolved in purified water. The total weight was 3744 g. The solution was adjusted to pH 7.0 with a 1 mol/L sodium hydroxide aqueous solution and filtered through a 0.2 μm filter.

In the resulting filtrate (1872 g), bulk aripiprazole monohydrate produced by batch crystallization (208 g; mean particle size of the bulk powder=386 μm; 10% diameter=118 μm; 50% diameter=356 μm; 90% diameter=1640 μm) was dispersed to form a primary suspension. The dispersion procedure for preparing the primary suspension was conducted by using a Three-One Motor (produced by HEIDON) for stirring with 50 mm-diameter blades at about 700 to 800 rpm.

The primary suspension was pulverized with Clearmix (CLM-1.5S) at 18000 rpm for 7.5 minutes per liter. As a result, a secondary suspension was obtained.

Without temperature control, the obtained secondary suspension was pulverized by passing 10 times through a high-pressure homogenizer at 600 bar by discrete-pass method. The mean particle size of the suspensions pulverized once and pulverized 10 times was measured with a particle size distribution analyzer (SALD-3000J, Shimadzu Corp.). The results are shown below.

TABLE 4

| Number of Times Pulverized | Mean Particle Size (μm) |
| --- | --- |
| 1 | 5.0 |
| 10 | 3.0 |

Table 4 shows that even without controlling the inlet temperature, an aripiprazole suspension with a mean particle size of about 3 to 5 μm can be prepared. When controlling the inlet temperature, an aripiprazole suspension with a mean particle size of less than 3 microns can be obtained (see Examples 1 and 2).

Example 5

Sodium carboxymethyl cellulose (45.76 g), 228.80 g of mannitol, and 4.07 g of sodium dihydrogen phosphate monohydrate were dissolved in purified water. The total weight was 5148 g. Sodium carboxymethyl cellulose with a viscosity of 93 cps (4% aqueous solution, 25° C.) and 187 cps (4% aqueous solution, 25° C.) were used for preparation. The solution was adjusted to pH 7.0 with a 1 mol/L sodium hydroxide solution and filtered through a 0.2 μm filter.

In the resulting filtrate (1872 g), bulk aripiprazole monohydrate produced by batch crystallization (208 g; mean particle size of the bulk powder=239 μm; 10% diameter=99 μm; 50% diameter=276 μm; 90% diameter=632 μm) was dispersed to form primary suspensions.

The primary suspensions were pulverized with Clearmix (CLM-1.5S) at 18000 rpm for 7.5 minutes per liter. As a result, secondary suspensions were obtained.

The obtained secondary suspensions were cooled so as to keep the inlet temperature at about 20° C., and pulverized by passing 10 times through a high-pressure homogenizer at 300 bar by discrete-pass method.

The mean particle size of the suspensions pulverized once and pulverized 10 times was measured with a particle size distribution analyzer (SALD-3000J, Shimadzu Corp.). The results are shown below.

TABLE 5

| Number of Times Pulverized | Mean Particle Size (μm) Viscosity of Sodium Carboxymethyl Cellulose | |
| --- | --- | --- |
| | 93 cps | 187 cps |
| 1 | 5.3 | 5.7 |
| 10 | 2.5 | 2.6 |

Table 5 reveals that in the second pulverization step, even though the pulverization pressure of the high-pressure homogenizer is 300 bar, the difference in CMCNa viscosity does not affect the pulverization, as in Example 3.

Example 6

Sodium carboxymethyl cellulose (183 g), 915 g of mannitol, and 16.3 g of sodium dihydrogen phosphate monohydrate were dissolved in purified water. The total weight was 20592 g. The solution was adjusted to pH 7.0 with a 1 mol/L sodium hydroxide aqueous solution and filtered through a 0.2 μm filter.

In the resulting filtrate (18720 g), bulk aripiprazole monohydrate produced by batch crystallization (2080 g; mean particle size of the bulk powder=246 μm; 10% diameter=103 μm; 50% diameter=260 μm; 90% diameter=548 μm) was dispersed to form a primary suspension.

The primary suspension was pulverized with Clearmix (CLM-9S) at 5700 rpm for 2.1 minutes per liter. As a result, a secondary suspension was obtained.

The obtained secondary suspension (500 mL) was recirculated through a high-pressure homogenizer, and cooled at the outlet of the high-pressure homogenizer to adjust the inlet temperature at about 15° C. to about 25° C. The suspension was pulverized for 32.5 minutes at a pulverization pressure of 500 bar, while being discharged from the high-pressure homogenizer at a rate of 155 mL/min.

The mean particle size of the suspensions pulverized for 3.25 minutes and 32.5 minutes was measured with a particle size distribution analyzer (SALD-3000J, Shimadzu Corp.). The results are shown below.

TABLE 6

| Pulverization Time (Minutes) | Mean Particle Size (μm) |
| --- | --- |
| 3.25 | 3.5 |
| 32.5 | 1.7 |

Table 6 shows that the desired pulverization is also possible by recirculation method, like pulverization by discrete-pass method as used in Examples 1 to 5. Additionally, it is seen that even when the pulverization by recirculation method is repeatedly performed over a long time, the mean particle size do not fall below 1 μm.

Example 7

Sodium carboxymethyl cellulose (45.76 g), 228.80 g of mannitol, and 4.07 g of sodium dihydrogen phosphate monohydrate were dissolved in purified water. The total weight was 5148 g. The solution was adjusted to pH 7.0 with a 1 mol/L sodium hydroxide aqueous solution and filtered through a 0.2 μm filter.

In the resulting filtrate (1872 g), bulk aripiprazole monohydrate produced by batch crystallization (208 g; mean particle size of the bulk powder=256 μm; 10% diameter=109 μm; 50% diameter=272 μm; 90% diameter=566 μm) was dispersed to form a primary suspension.

The primary suspension was pulverized using Clearmix (CLM-1.5S) at 18000 rpm for 7.5 minutes per liter. As a result, a secondary suspension was obtained.

The obtained secondary suspension (500 mL) was cooled so as to keep the inlet temperature at about 20° C., and pulverized by passing four times through a high-pressure homogenizer at 500 bar. Subsequently, the suspension was circulated through a high-pressure homogenizer, and cooled at the outlet of the high-pressure homogenizer to adjust the inlet temperature at about 20° C. The suspension was further pulverized by recirculation method for 42 minutes at a pulverization pressure of 500 bar, while being discharged at a rate of 155 mL/min.

The mean particle size of the suspensions pulverized once, pulverized four times by discrete-pass method, and pulverized four times by discrete-pass method and further pulverized for 42 minutes by recirculation method was measured with a particle size distribution analyzer (SALD-3000J, Shimadzu Corp.). The results are shown below.

TABLE 7

| Number of Times Pulverized, or Pulverization Time | Mean Particle Size (μm) |
| --- | --- |
| 1 | 4.0 |
| 4 | 2.6 |
| 42 Minutes after Four-Time Pulverization[1] | 1.6 |

[1]The suspension was pulverized four times by discrete-pass method and further pulverized for 42 minutes by recirculation method.

Table 7 shows that the discrete-pass method may be combined with the recirculation method. Moreover, even when the recirculation pulverization is repeatedly performed over a long time, the mean particle size do not fall below 1 μm.

Example 8

Sodium carboxymethyl cellulose (450 g), 2250 g of mannitol, 40 g of sodium dihydrogen phosphate monohydrate, and 160 g of a 1 mol/L sodium hydroxide aqueous solution were dissolved in purified water. The total weight was 50625 g. The solution was filtered through a 0.2 μm filter. In the filtrate (748.8 g), bulk aripiprazole monohydrate produced by batch crystallization (83.2 g; mean particle size of the bulk powder=256 μm; 10% diameter=109 μm; 50% diameter=272 μm; 90% diameter=566 μm) was dispersed to form a primary suspension.

The primary suspension was pulverized with a dispersion machine that applies shear force to a material to be processed (trade name: "T-50 Basic", produced by IKA Japan, Inc.) using a shaft available under the generic name of shaft generator (trade name: "S50N-G45G", produced by IKA Japan, Inc.) at 6400 rpm for 7.5 minutes per liter. As a result, a secondary suspension was obtained.

The obtained secondary suspension was cooled so as to keep the inlet temperature at about 20° C., and pulverized five times in total by passing through a high-pressure homogenizer once at 300 bar and four times at 500 bar by discrete-pass method. The mean particle size of the suspensions pulverized once and pulverized five times was measured with a particle size distribution analyzer (SALD-3000J, Shimadzu Corp.). The results are shown below.

TABLE 8

| Number of Times Pulverized | Mean Particle Size (μm) |
| --- | --- |
| 1 | 6.4 |
| 5 | 2.7 |

Table 8 indicates that any pulverizing machines may be used for the first pulverization as long as they have some degree of shear force to pulverize bulk powder. Not only the aforementioned high shear homomixers (e.g., Clearmix) but also dispersion machines (e.g., "T-50 Basic", produced by IKA Japan, Inc.) are usable.

Example 9

Sodium carboxymethyl cellulose (450 g), 2250 g of mannitol, 40 g of sodium dihydrogen phosphate monohydrate, and 160 g of a 1 mol/L sodium hydroxide aqueous solution were dissolved in purified water. The total weight was 50625 g. The solution was filtered through a 0.2 μm filter. In the filtrate (748.8 g), bulk aripiprazole monohydrate produced by batch crystallization (83.2 g; mean particle size of the bulk powder=256 μm; 10% diameter=109 μm; 50% diameter=272 μm; 90% diameter=566 μm) was dispersed to form a primary suspension.

The primary suspension was cooled so as to keep the inlet temperature at about 20° C., and pulverized six times in total by discrete-pass method by passing through a high-pressure homogenizer once at 100 bar (first pulverization step), and once at 300 bar and four times at 500 bar (second pulverization step). The mean particle size of the suspensions pulverized once, pulverized twice, and pulverized six times was measured with a particle size distribution analyzer (SALD-3000J, Shimadzu Corp.). The results are shown below.

TABLE 9

| Number of Times Pulverized | Mean Particle Size (μm) |
| --- | --- |
| 1 | 18.6 |
| 2 | 4.7 |
| 6 | 2.4 |

Table 9 shows that even a high-pressure homogenizer can be used for the first pulverization step without inducing clogging in the line, if a lower pulverization pressure is used.

Example 10

Sodium carboxymethyl cellulose (16.64 g), 83.20 g of mannitol, and 1.48 g of sodium dihydrogen phosphate monohydrate were dissolved in purified water. The total weight was 3704 g. The solution was adjusted to pH 7.0 with a 1 mol/L sodium hydroxide aqueous solution and filtered through a 0.2 μm filter.

In the resulting filtrate (1852 g), bulk aripiprazole monohydrate produced by batch crystallization (208 g; mean particle size of the bulk powder=238 μm; 10% diameter=72 μm; 50% diameter=274 μm; 90% diameter=811 μm) was dispersed to form a primary suspension.

The primary suspension was pulverized with Clearmix (CLM-1.5S) at 18000 rpm for 7.5 minutes per liter. As a result, a secondary suspension was obtained.

Without temperature control, the obtained secondary suspension was pulverized by passing 10 times through a high-pressure homogenizer at 600 bar by discrete-pass method. The mean particle size of the suspensions pulverized once and pulverized 10 times was measured with a particle size distribution analyzer (SALD-3000J, Shimadzu Corp.). The results are shown below.

TABLE 10

| Number of Times Pulverized | Mean Particle Size (μm) |
| --- | --- |
| 1 | 4.5 |
| 10 | 3.4 |

Table 10 indicates that even without controlling the inlet temperature, an aripiprazole suspension with a mean particle size of about 3 to 5 μm can be prepared. When controlling the inlet temperature, an aripiprazole suspension with a mean particle size of less than 3 microns can be obtained (see Example 11 below).

Example 11

Sodium carboxymethyl cellulose (16.64 g), 83.20 g of mannitol, and 1.48 g of sodium dihydrogen phosphate monohydrate were dissolved in purified water. The total weight was 3704 g. The solution was adjusted to pH 7.0 with a 1 mol/L sodium hydroxide aqueous solution and filtered through a 0.2 μm filter.

In the resulting filtrate (1852 g), bulk aripiprazole monohydrate produced by batch crystallization (208 g; mean particle size of the bulk powder=238 μm; 10% diameter=72 μm; 50% diameter=274 μm; 90% diameter=811 μm) was dispersed to form a primary suspension.

The primary suspension was pulverized with Clearmix (CLM-1.5S) at 18000 rpm for 7.5 minutes per liter. As a result, a secondary suspension was obtained.

The obtained secondary suspension was cooled so as to keep the inlet temperature at about 20° C., and pulverized by passing 10 times through a high-pressure homogenizer at 600 bar by discrete-pass method.

The mean particle size of the suspensions pulverized once and pulverized 10 times was measured with a particle size distribution analyzer (SALD-3000J, Shimadzu Corp.). The results are shown below.

TABLE 11

| Number of Times Pulverized | Mean Particle Size (μm) |
| --- | --- |
| 1 | 4.6 |
| 10 | 1.9 |

Table 11 indicates that even when the concentration of CMCNa as a suspending agent is low, first pass allows the preparation of a suspension with a mean particle size of 1 to 5 μm, and 10-time passing allows the preparation of a suspension with a mean particle size of 2 μm.

Example 12

Sodium carboxymethyl cellulose (16.64 g), 83.20 g of mannitol, and 1.48 g of sodium dihydrogen phosphate monohydrate were dissolved in purified water. The total weight was 3704 g. The solution was adjusted to pH 7.0 with a 1 mol/L sodium hydroxide aqueous solution and filtered through a 0.2 μm filter.

In the resulting filtrate (1852 g), bulk aripiprazole monohydrate produced by batch crystallization (208 g; mean particle size of the bulk powder=258 μm; 10% diameter=99 μm; 50% diameter=280 μm; 90% diameter=609 μm) was dispersed to form a primary suspension.

The primary suspension was pulverized with Clearmix (CLM-1.5S) at 18000 rpm for 7.5 minutes per liter. As a result, a secondary suspension was obtained.

The obtained secondary suspension was cooled or warmed so as to keep the inlet temperature at about 10° C., about 20° C., about 40° C., and about 60° C., and pulverized by passing 10 times through a high-pressure homogenizer at 600 bar by discrete-pass method. The mean particle size of the suspensions pulverized once and pulverized 10 times was measured with a particle size distribution analyzer (SALD-3000J, Shimadzu Corp.). The results are shown below.

TABLE 12

| Number of Times Pulverized | Mean Particle Size (μm) | | | |
| --- | --- | --- | --- | --- |
| | 10° C. | 20° C. | 40° C. | 60° C. |
| 1 | 4.6 | 4.4 | 4.5 | 4.7 |
| 10 | 1.8 | 2.1 | 2.3 | 4.2 |

Table 12 indicates the following:
(i) Even when the concentration of CMCNa is low, a suspension with a mean particle size of 1 to 5 μm can be prepared as in Example 1.
(ii) Even when the concentration of CMCNa is low, a suspension with a mean particle size of 2 to 3 μm can be prepared as in Example 1, by adjusting the inlet temperature to 40° C. or less.

Example 13

Sodium carboxymethyl cellulose (8.32 g), 41.60 g of mannitol, and 0.74 g of sodium dihydrogen phosphate monohydrate were dissolved in purified water. The total weight was 1852 g. The solution was adjusted to pH 7.0 with a 1 mol/L sodium hydroxide aqueous solution and filtered through a 0.2 μm filter.

In the obtained filtrate (740.8 g), bulk aripiprazole monohydrate produced by batch crystallization (83.2 g; mean particle size of the bulk powder=256 μm; 10% diameter=99 μm; 50% diameter=280 μm; 90% diameter=609 μm) was dispersed to form a primary suspension. The dispersion procedure for preparing the primary suspension was conducted by using Three One Motor (produced by HEIDON) for stirring with 50 mm-diameter blades at about 300 to 500 rpm.

The primary suspension was pulverized with Clearmix (CLM-1.5S) at 18000 rpm for 7.5 minutes per liter. As a result, a secondary suspension was obtained.

The obtained secondary suspension (450 mL) was circulated through a high-pressure homogenizer, and cooled at the outlet of the high-pressure homogenizer to adjust the inlet temperature at about 20° C.

The suspension was pulverized by recirculation method for 72.5 minutes at a pulverization pressure of 500 bar, while being discharged from the high-pressure homogenizer at a rate of 155 mL/min. The mean particle size of the suspensions pulverized for 14.5 minutes and pulverized for 72.5 minutes was measured with a particle size distribution analyzer (SALD-3000J, Shimadzu Corp.). The results are shown below.

TABLE 13

| Pulverization Time (Minutes) | Mean Particle Size (μm) |
|---|---|
| 14.5 | 2.2 |
| 72.5 | 1.5 |

Table 13 shows that even though the concentration of CMCNa is low, the desired pulverization is possible by recirculation method; additionally, even when the recirculation pulverization is repeatedly performed over a long time, the mean particle size do not fall below 1 μm.

Example 14

Each of aripiprazole suspensions obtained by the method shown in Examples 1 to 13 (2.5 mL) was poured into a glass vial, and the vial was partially stoppered with a rubber stopper. The vials were transferred to a freeze-dryer and lyophilized under the following conditions:

(a) Freezing: The vials were cooled to −40° C. at 1° C./min., and then kept at −40° C. for 6 hours;

(b) Drying: The chamber pressure was lowered to about 13 Pa, and the shelf temperature of the freeze-dryer was increased to −5° C. at a rate of 0.3° C./min.; drying was then continued for 55.5 hours while the degree of vacuum was kept at about 13 Pa, and the shelf temperature kept at about −5° C.;

(c) The vials were stoppered under atmospheric pressure or partial vacuum using nitrogen or air, and then removed from the freeze-dryer; and (d) The vials were sealed with aluminum seals.

The aripiprazole each of the resulting freeze-dried aripiprazole suspensions was Hydrate A.

Example 15

Each of the aripiprazole suspensions obtained by the method shown in Examples 1 to 13 was poured into a glass vial, and the vial was partially stoppered with a rubber stopper. The vials were transferred to a freeze-dryer and lyophilized under the following conditions:

(a) Freezing: The vials were cooled to −40° C. at 1° C./min., and then kept at −40° C. for 6 hours;

(b) Primary drying: The chamber pressure was lowered to about 13 Pa, and the shelf temperature of the freeze-dryer was increased to −5° C. at a rate of 0.3° C./min.; primary drying was then continued for 55.5 hours while the degree of vacuum was kept at about 13 Pa, and the shelf temperature kept at about −5° C.;

(c) Secondary drying: The shelf temperature was increased to 25° C., and drying continued for 24 hours while the degree of vacuum was kept at about 13 Pa; the shelf temperature was then increased to 50° C., and drying continued for 24 hours while the degree of vacuum was kept at about 13 Pa;

(d) The vials were stoppered under atmospheric pressure or partial vacuum using nitrogen or air, and then removed from the freeze-dryer; and (e) The vials were sealed with aluminum seals.

The aripiprazole each of the resulting freeze-dried aripiprazole suspensions was in the anhydrous form.

The invention claimed is:

1. A method for producing an aripiprazole suspension comprising the steps of:
   (a) combining bulk aripiprazole and a vehicle to form a primary suspension;
   (b) subjecting the primary suspension to a first pulverization to form a secondary suspension; and
   (c) subjecting the secondary suspension to a second pulverization to form a final suspension,
   wherein in the first pulverization of step (b), the secondary suspension is formed by pulverizing the primary suspension using a high shear pulverizing machine or a dispersion machine that applies shear force to a material to be processed, and in the second pulverization of step (c), the final suspension is formed by pulverizing the secondary suspension using a high-pressure homogenizer with an inlet temperature ranging from about 1° C. to about 70° C.

2. The method according to claim 1, wherein in step (c), the high-pressure homogenizer is used at a pulverization pressure of 300 to 1000 bar.

3. The method according to claim 1, wherein in step (c), the high-pressure homogenizer is used at a pulverization pressure of 300 to 600 bar.

4. A method for producing an aripiprazole suspension comprising the steps of:
   (a) combining bulk aripiprazole and a vehicle to form a primary suspension;
   (b) subjecting the primary suspension to a first pulverization to form a secondary suspension; and
   (c) subjecting the secondary suspension to a second pulverization to form a final suspension,
   wherein in the first pulverization of step (b), the secondary suspension is formed by pulverizing the primary suspension using a high-pressure homogenizer at a pulverization pressure of 50 to 200 bar, and in the second pulverization of step (c), the final suspension is formed by pulverizing the secondary suspension using a high-pressure homogenizer at a pulverization pressure of 200 to 1000 bar, wherein the difference between the pulverization pressure in step (b) and the pulverization pressure in step (c) is 100 to 900 bar, and wherein in steps (b) and (c), the high-pressure homogenizer is used with an inlet temperature ranging from about 1° C. to about 70° C.

5. The method according to claim 1 or 4, wherein the bulk aripiprazole contains aripiprazole particles with a particle size of 100 μm or more in an amount of 10% or more, and has a mean particle size of 20 μm to 1000 μm.

6. The method according to claim 1 or 4, wherein the bulk aripiprazole has a mean particle size of more than 100 μm.

7. The method according to claim 1 or 4, wherein the bulk aripiprazole has a mean particle size of 110 μm to 1000 μm.

8. The method according to claim 1 or 4, wherein the bulk aripiprazole has a mean particle size of 200 μm to 400 μm.

9. The method according to claim 1 or 4, wherein the aripiprazole in the aripiprazole suspension has a mean particle size of 1 to 10 μm.

10. The method according to claim 1 or 4, wherein the aripiprazole in the aripiprazole suspension has a mean particle size of 1 to 5 μm.

11. The method according to claim 1 or 4, wherein the aripiprazole in the aripiprazole suspension has a mean particle size of 2 to 4 μm.

12. The method according to claim 1 or 4, wherein the aripiprazole in the aripiprazole suspension has a mean particle size of 2 to 3 μm.

13. The method according to claim 1, comprising the steps of:
(I) combining sterile bulk aripiprazole with a mean particle size of 200 μm to 400 μm and a sterile vehicle to form a sterile primary suspension;
(II) subjecting the sterile primary suspension to first pulverization using a high shear pulverizing machine or a dispersion machine that applies shear force to a material to be processed, to form a sterile secondary suspension; and
(III) subjecting the sterile secondary suspension to second pulverization using a high-pressure homogenizer to form a sterile final suspension;
wherein the aripiprazole in the sterile final suspension has a mean particle size of 1 to 10 μm.

14. The method according to claim 1 or 4, wherein the bulk aripiprazole is in the form selected from the group consisting of monohydrate and Anhydride Crystals B.

15. The method according to claim 1 or 4, further comprising the step of filtering the final suspension with a filter having a nominal filtration rating of 10 to 225 μm.

16. The method according to claim 1 or 4, wherein the vehicle contains at least one suspending agent selected from the group consisting of carboxymethyl cellulose, carboxymethyl cellulose salts, hydroxypropyl cellulose, hydroxypropylethyl cellulose, hydroxypropylmethyl cellulose and polyvinyl pyrrolidone.

17. The method according to claim 4, wherein in step (b), the pulverization pressure of the high-pressure homogenizer is in the range of 50 to 200 bar, and in step (c), the pulverization is carried out plural times and the pulverization pressure is raised stepwise within the range of 200 to 1000 bar.

18. The method according to claim 17, wherein in step (c), the final pulverization pressure of the high-pressure homogenizer is 300 to 600 bar.

19. The method according to claim 4, wherein in steps (b) and (c), the high-pressure homogenizer is used at an inlet temperature from about 1° C. to about 50° C.

20. A method for producing an aripiprazole suspension comprising the steps of:
(a) combining bulk aripiprazole and a vehicle to form a primary suspension;
(b) subjecting the primary suspension to first pulverization to form a secondary suspension having a particle size in the range of 5 to 100 μm; and
(c) subjecting the secondary suspension to second pulverization to form a final suspension,
wherein in the first pulverization of step (b), the secondary suspension is formed by pulverizing the primary suspension using a high shear pulverizing machine or a dispersion machine that applies shear force to a material to be processed, and in the second pulverization of step (c), the final suspension is formed by pulverizing the secondary suspension using a high-pressure homogenizer with an inlet temperature ranging from about 1° C. to about 70° C.

* * * * *